A jaw implant comprising a cylindrical, hollow body, threaded on its inner and outer side, and a threaded member in the body acting on horizontally slidable retention pins. The retention pins, subcortically driven into the spongiosa of the jaw bone, are chamferred in such a manner that the longer sides thereof are directed toward the implant support. The edges on the longer sides, at the internal end of the pins, are chamferred for cooperating with the tapered end of the threaded member.

United States Patent [19]

Prezmecky

[11] Patent Number: 5,013,242
[45] Date of Patent: May 7, 1991

[54] JAW IMPLANT

[76] Inventor: László Prezmecky, Grundackerstrasse 20/E, CH-4414 Füllinsdorf, Switzerland

[21] Appl. No.: 274,186

[22] Filed: Nov. 22, 1988

[30] Foreign Application Priority Data

Nov. 26, 1987 [EP] European Pat. Off. ........ 87810699.6

[51] Int. Cl.⁵ .............................................. A61C 8/00
[52] U.S. Cl. ..................................... 433/174; 433/173
[58] Field of Search ...................... 433/173, 174, 175

[56] References Cited

U.S. PATENT DOCUMENTS

| 2,745,180 | 5/1956 | Kiernan | 433/175 |
| 2,857,670 | 10/1958 | Kiernan | 433/175 |
| 3,497,953 | 3/1970 | Weissman | 433/173 |
| 4,044,468 | 8/1977 | Kahn | 433/102 |
| 4,523,587 | 6/1985 | Frey | 433/173 |

FOREIGN PATENT DOCUMENTS

| 0136532 | 4/1985 | European Pat. Off. | ........... 433/173 |
| 3421056 | 12/1985 | Fed. Rep. of Germany . | |
| 2119258 | 11/1983 | United Kingdom | ............... 433/174 |

*Primary Examiner*—John J. Wilson
*Assistant Examiner*—Adriene B. Lepiane
*Attorney, Agent, or Firm*—Marks Murase & White

[57] ABSTRACT

A jaw implant comprising a cylindrical, hollow body, threaded on its inner and outer side, and a threaded member in the body acting on horizontally slidable retention pins. The retention pins, subcortically driven into the spongiosa of the jaw bone, are chamferred in such a manner that the longer sides thereof are directed toward the implant support. The edges on the longer sides, at the internal end of the pins, are chamferred for cooperating with the tapered end of the threaded member.

The implant can be reliably secured even in thin jaw bones, in particular of aged patients.

7 Claims, 2 Drawing Sheets

JAW IMPLANT

BACKGROUND OF THE INVENTION

The present invention relates to a jaw implant, having a hollow body threaded on its inner side, said body comprising a threaded member acting on horizontally slidable pins.

Such an implant is for example disclosed in U.S. Pat. No. 2,745,180, whereby a thimble, driven by a screw element drives four cylindrical pins with a tapered end into the bone. The inner end of the retention pins is also symmetrically tapered, and the outer surface of the body is relatively smooth and tapered. The smooth surface of the body and the symmetrically tapered ends of the retention pins lead to an insufficient anchorage of the implant. The contact line between the tapered end of the thimble and the tapered end of the retention pins transmits forces poorly.

U.S. Pat. No. 2,857,670 discloses a similar implant, having a multitude of retention pins in different levels, thus complicating very much the fabrication of such small implants and necessitating an enormous precision of the parts.

U.S. Pat. No. 3,497,953 discloses a similar implant, wherein four bendable elements are driven by a complicated mechanism into the bone. In view of the small dimensions of such implants the bendable elements and the driving mechanism are critical parts, leading to a costly production.

German Offenlegungsschrift No. 3,421,056 discloses a jaw implant with a cylindrical full body having supporting ribs at its surface. This type of implant needs a long body for sufficient anchorage and is not suited for patients with thin jaw bones.

SUMMARY OF THE INVENTION

It is therefore the object of the present invention to provide for a jaw implant with increased anchoring ability. This object is attained with a jaw implant, wherein its body is cylindrical and externally threaded and the retention pins, subcortically driven into the spongiosa of the jaw bone, are chamferred in such a manner that the longer sides thereof are facing toward the implant support, and wherein the edges on said longer sides at the internal end of said pins are chamferred for cooperating with the correspondingly tapered end of said threaded member.

BRIEF DESCRIPTION OF THE DRAWINGS

The invention will be described further by way of an example with reference to the accompanying drawings, in which.

DESCRIPTION OF THE PREFERRED EMBODIMENT

Figure 1:
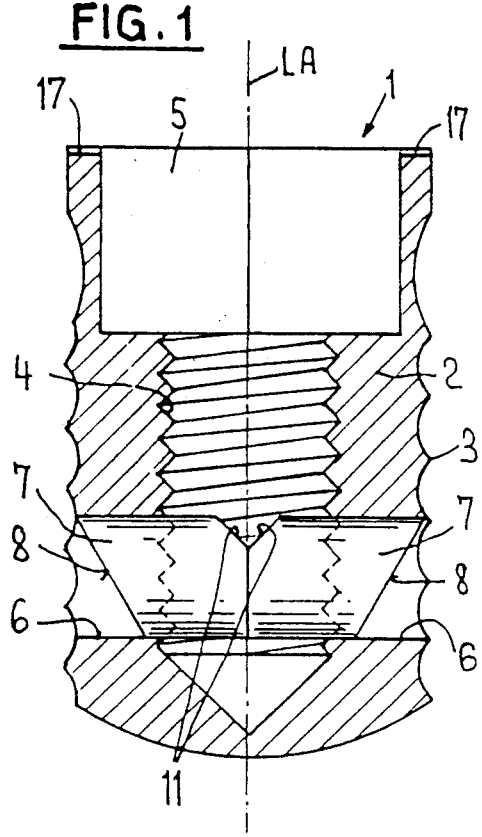
FIG. 1 shows in a longitudinal section the jaw implant according to the invention before its implantation.
Figure 2:
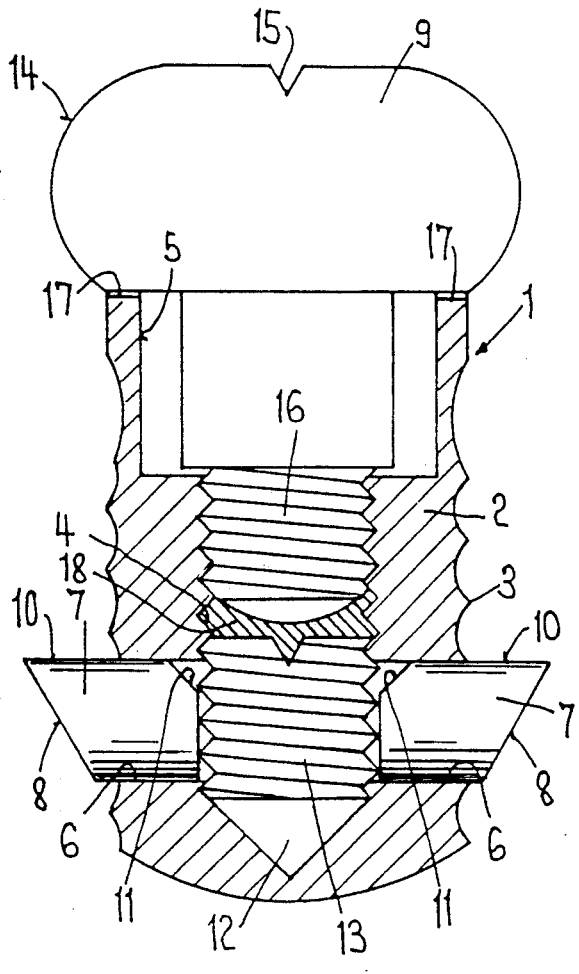
FIG. 2 shows the implant according to FIG. 1 after implantation and with an implant support.
Figure 3:
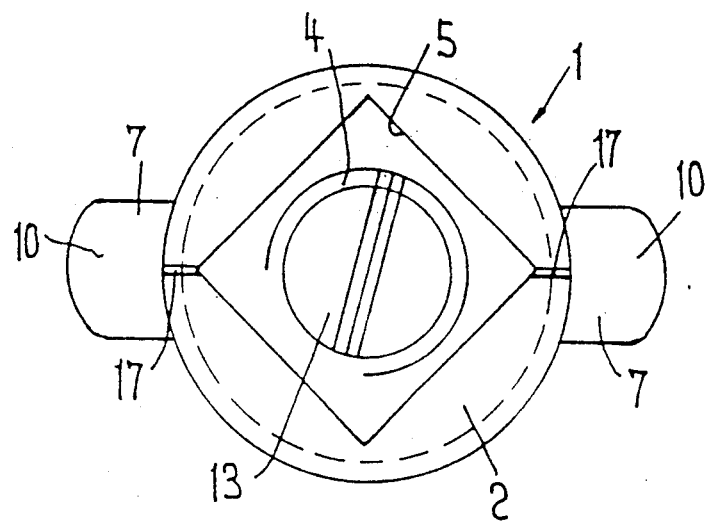
FIG. 3 shows the jaw implant according to FIG. 1 seen from above.
Figure 4:
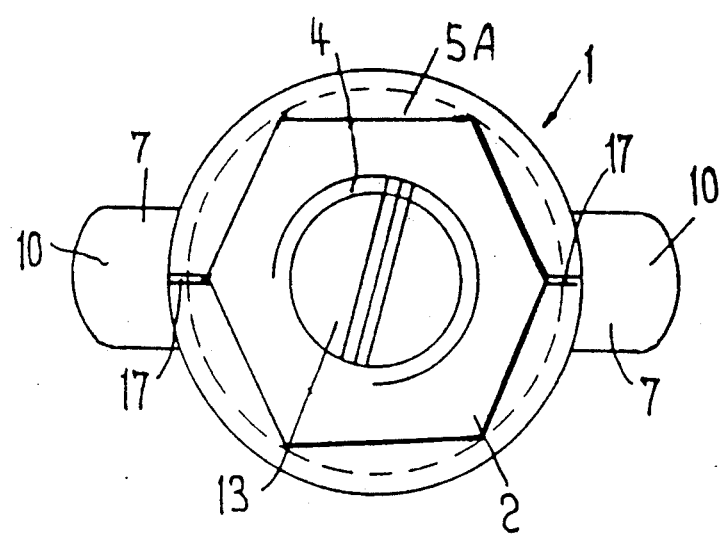
FIG. 4 shows an embodiment of the jaw implant seen from above.

FIG. 1 shows the jaw implant 1 with a hollow, sleeve-like, cylindrical body 2 having an external thread or ribs 3 for being screwed into the jaw bone. Cylindrical implants have a better retention force against the suction created by the chewing movements. The interior of the body is provided with an internal thread 4 and a rectangular opening 5 at its top for the insertion of a tool. The opening 5 can also be hexagonal. See opening 5A in FIG. 4. The lower part of the body is provided with a crosshole 6 perpendicular to the longitudinal axis LA of the body, in which crosshole two retention pins 7 are loosely inserted. The outer ends 8 of the retention pins are chamferred or bevelled thus, that the sides 10 facing towards the implant support, see FIG. 2, are longer than its undersides. The interior upper edges 11 of the retention pins are also chamferred, as follows from FIG. 1. Thus the tapered end 12 of the threaded member 13 cooperates with the two chamferred edges of the pins and, due to its form, is able to transmit efficiently the driving force needed to drive the pins into the jaw bone, as shown in FIG. 2.

It is important for an efficient anchorage that the distance between the upper side 10 of the retention pins and the upper rim of the body is great enough to ensure that these upper sides of the pins are located beneath the hard corticalis and that the retention pins are driven into the relatively softer spongiosa. In an example of an implant of a height of 10 mm, the distance between the upper side 10 of the pins and the upper rim of the body is about 6 mm. The diameter of this example is about 6 mm.

The implant support 9 is provided with a spherical surface 14 with a slit 15 for screwing in the threaded shaft 16 thereof into the internal thread 4 of the body. The prosthesis or prosthesis support can be fastened by suction-cup-like, elastic means on the implant support.

For implanting the implant, first a core hole is drilled with a bone cutter. The hole's diameter is less than the diameter of the implant body. For example, a hole 5 mm in diameter would be drilled if a body of 6 mm in diameter is used. The hole's depth would be about 1 mm greater than the length of the implant. Then, the body is screwed in with the aid of a tool inserted in opening 5 of the body. A threaded member 13 is screwed in to drive the retention pins 7 outward about 1.5 mm. The outer surface of the body can be provided with longitudinal grooves, for forming a self-cutting thread or for enhancing the cutting effect of the thread.

Since the retention pins are loosely inserted in the implant body it is imperative to put in the threaded member before screwing in the implant body, to block the retention pins. For insuring a reliable operating of the retention pins they must be fitted exactly. When in final position, the pin's inner sides rest against the threads of the threaded member 13. The inner sides of the pins are perpendicular to a longitudinal axis through the pins. After the anchorage of the body a healing cap is put on top of it, having a threaded shaft insertable into thread 4 of the body. After healing the implant support is fastened into the implant body. To prevent the penetration of pathogenic agents a closure 18 which is impermeable to bacteria, for example of elastic rubber, is put between the head of the threaded member 13 and the threaded shaft 16.

If the implant is meant to serve for the fastening of other supports, it is possible to manufacture on the base of the above described implant a lab implant, or another implant support can be screwed in, in which another threaded shaft can be fastened, which is provided with a gold cap and serves as holder for a removable bar.

Any known material can be used for the implants, for example metal or precious metal alloys as well as titanium or ceramics. It is also possible to foresee more than two retention pins, for example four.

In order to adjust the implant body in relation to the retention pins, two marks 17 are provided on the upper rim of the implant body, facing the direction of the pins.

The above description shows further advantages of the implant, such as very simple instrumentation, needing only a simple X-ray apparatus which is installed in every dental practice. Further, the implantation technic for the above described implant needs no special training.

I claim:

1. A jaw implant comprising:
   a substantially cylindrical body having exterior sides and intersecting vertical and horizontal bores, the vertical bore and the exterior sides being substantially threaded,
   at least one retention pin adapted to be inserted into the horizontal bore and having top, bottom, outer and inner sides and an upper inner corner, said retention pin being bevelled at its outer side so that its bottom side is shorter than its top side and chamferred at its upper inner corner, the inner side being perpendicular to a longitudinal axis through said pin, and
   a substantially cylindrical, externally threaded member having a lower end which is tapered to a point so that when moved into the vertical bore, it cooperates with the upper inner corner of said retention pin, forcing said retention pin outward so that the inner side of said pin rests on the external threads of said cylindrical member.

2. A jaw implant according to claim 1, further comprising a closure impermeable to bacteria, said closure being adapted to be positioned on top of said cylindrical member when said cylindrical member is inserted in the vertical bore so as to seal said cylindrical member in said cylindrical body, and
   an implant support having a cap and a threaded shaft, the cap being positioned directly above the shaft, said support being adapted to be screwed into said cylindrical body so as to rest on top of said closure.

3. A jaw implant according to claim 1, wherein said body further comprises a plug-in opening for receiving a tool for threading said body into a jaw bone, said plug-in opening being rectangular in shape and located directly above the vertical bore.

4. A jaw implant according to claim 1, wherein said body further comprises a plug-in opening for receiving a tool for threading said body into a jaw bone, said plug-in opening being hexagonal in shape and located directly above the vertical bore.

5. A jaw implant according to claim 3 or claim 4, wherein said body has an upper rim provided on its top.

6. A jaw implant according to claim 5, wherein said rim has at least one downwardly directed mark.

7. A jaw implant according to claim 5, wherein said rim has a means for adjusting said jaw implant in relation to said retention pins.

* * * * *